United States Patent [19]
Kanda

[11] Patent Number: 6,123,669
[45] Date of Patent: Sep. 26, 2000

[54] 3D ULTRASOUND IMAGING USING 2D ARRAY

[75] Inventor: Ryoichi Kanda, Otawara, Japan

[73] Assignee: Kabushiki Kaisha Toshiba, Kawasaki, Japan

[21] Appl. No.: 09/167,501

[22] Filed: Oct. 7, 1998

[30] Foreign Application Priority Data

May 13, 1998 [JP] Japan .................................. 10-130430

[51] Int. Cl.[7] ...................................................... A61B 8/00
[52] U.S. Cl. .......................... 600/443; 128/916; 128/147; 600/447
[58] Field of Search ..................................... 600/437, 443, 600/444, 447; 128/916; 367/7, 11, 138

[56] References Cited

U.S. PATENT DOCUMENTS

| | | |
|---|---|---|
| 4,694,434 | 9/1987 | von Ramm et al. . |
| 5,546,807 | 8/1996 | Oxaal et al. . |
| 5,655,535 | 8/1997 | Friemel et al. .......................... 128/916 |
| 5,793,701 | 8/1998 | Wright et al. ............................... 367/7 |
| 5,856,955 | 1/1999 | Cole et al. ............................... 367/138 |
| 5,865,750 | 2/1999 | Hatfield et al. .......................... 128/916 |
| 5,879,303 | 3/1999 | Averkiou et al. ....................... 600/447 |
| 5,899,863 | 5/1999 | Hatfield et al. .......................... 600/443 |
| 5,910,818 | 6/1999 | Paik et al. ............................... 348/222 |

*Primary Examiner*—Marvin M. Lateef
*Assistant Examiner*—Ali M. Imam
*Attorney, Agent, or Firm*—Oblon, Spivak, McClelland, Maier & Neustadt, P.C.

[57] ABSTRACT

A three-dimensional imaging method using an ultrasound wave enables a region of interest to be extracted through threshold processing. The method above has its image readily adversely affected and the technique has not yet been too much advanced from the practical viewpoint. By creating an image based on the harmonics components contained in an echo signal it is possible to acquire a high image quality and to advance a practical application of the three-dimensional imaging by the ultrasound wave. The harmonics wave is produced in proportion to sound pressure. That is, the higher the sound pressure, more harmonics components are produced. As a result, the ultrasound beam is effectively narrowed and the spatial resolution is improved. Since the harmonics components are not too much produced from a grating lobe lower in sound pressure than a main lobe, the production of the grating lobe is effectively suppressed, so that an image quality is prominently improved.

7 Claims, 11 Drawing Sheets

|   | COLUMN NUMBER | | | | | | | | | |
|---|---|---|---|---|---|---|---|---|---|---|
|   | 1 | 2 | 3 | 4 | - | - | - | - | - | m |
| 1 | 1 | 2 | 1 | 2 | 1 | 2 | 1 | 2 | 1 | 2 |
| 2 | 3 | 4 | 3 | 4 | 3 | 4 | 3 | 4 | 3 | 4 |
| 3 | 1 | 2 | 1 | 2 | 1 | 2 | 1 | 2 | 1 | 2 |
| 4 | 3 | 4 | 3 | 4 | 3 | 4 | 3 | 4 | 3 | 4 |
|   | 1 | 2 | 1 | 2 | 1 | 2 | 1 | 2 | 1 | 2 |
|   | 3 | 4 | 3 | 4 | 3 | 4 | 3 | 4 | 3 | 4 |
|   | 1 | 2 | 1 | 2 | 1 | 2 | 1 | 2 | 1 | 2 |
|   | 3 | 4 | 3 | 4 | 3 | 4 | 3 | 4 | 3 | 4 |
|   | 1 | 2 | 1 | 2 | 1 | 2 | 1 | 2 | 1 | 2 |
| n | 3 | 4 | 3 | 4 | 3 | 4 | 3 | 4 | 3 | 4 |

GROUP 1; ODD-LINE, ODD-COLUMN
2; ODD-LINE, EVEN-COLUMN
3; EVEN-LINE, ODD-COLUMN
4; EVEN-LINE, EVEN-COLUMN

| | COLUMN NUMBER | | | | | | | | | |
|---|---|---|---|---|---|---|---|---|---|---|
| | 1 | 2 | 3 | 4 | — | — | — | — | — | m |
| 1 | 1 | 2 | 3 | 4 | 1 | 2 | 3 | 4 | 1 | 2 |
| 2 | 3 | 4 | 1 | 2 | 3 | 4 | 1 | 2 | 3 | 4 |
| 3 | 2 | 1 | 3 | 4 | 2 | 1 | 3 | 4 | 2 | 1 |
| 4 | 4 | 3 | 1 | 2 | 4 | 3 | 1 | 2 | 4 | 3 |
| ı | 1 | 2 | 3 | 4 | 1 | 2 | 3 | 4 | 1 | 2 |
| ı | 3 | 4 | 1 | 2 | 3 | 4 | 1 | 2 | 3 | 4 |
| ı | 2 | 1 | 3 | 4 | 2 | 1 | 3 | 4 | 2 | 1 |
| ı | 4 | 3 | 1 | 2 | 4 | 3 | 1 | 2 | 4 | 3 |
| ı | 1 | 2 | 3 | 4 | 1 | 2 | 3 | 4 | 1 | 2 |
| n | 3 | 4 | 1 | 2 | 3 | 4 | 1 | 2 | 3 | 4 |

3D ULTRASOUND IMAGING USING 2D ARRAY

BACKGROUND OF THE INVENTION

The present invention relates to an ultrasound diagnostic apparatus for scanning a three-dimensional region in an inside of a human subject (patient) with an ultrasound and creating a three-dimensional image in real-time on the basis of an echo signal obtained to allow it to be displayed.

The so-called three-dimensional scanning method for scanning a three-dimensional region in the inside of the human subject is typically divided into two methods. One method adopts a two-dimensional array type probe with a plurality of transducer elements arranged as a matrix array and moves an ultrasound beam vertically and horizontally across the three-dimensional region by an electronic operation, that is, a delay operation. The other method moves a one-dimensional array type probe manually or mechanically.

In order to scan the whole three-dimensional region for a short time period of, for example, 1/30 sec, while maintaining this in real-time, the former method is considered to become a mainstream in the future.

For the inspection of the circulatory system, in particular, the heart, such real-time three-dimensional imaging provides a three-dimensional configuration of the cardiac muscle, as well as information helpful to its motion and cardiac cavity volume, etc., to the observer. It is, therefore, expected that the diagnostic precision is remarkably improved. However, this method has few problems, that must be solved in order to obtain practical use.

Its major obstacle lies in that the ultrasound image is low in quality. In order to three-dimensionally display a region of interest of the heart, etc., with the use of a surface model and polygon model, it is necessary to have a process for extracting a contour of the region of interest. However, too low a quality of the ultrasound image causes many more extraction errors.

There are broadly two reasons for the low quality of ultrasound images obtained. One reason is that there occurs an artifact, that is, a false image, in the ultrasound image specific to, and not visible to, the X-ray computed tomography and magnetic resonance imaging. The generation of the artifact is due to the grating lobe, multiple reflection, lens effect in the patient, mirror effect, and so on. Another reason is that, due to the diffusion of the ultrasound, the temporal resolution of the ultrasound image is prominently degraded in comparison with the X-ray computed tomography and magnetic resonance imaging.

The two-dimensional array type probe indispensable to a three-dimensional real-time imaging involves much more transducer elements than the one-dimensional array type probe. If any channel is allocated individually to these transducer elements, the size of a transmitting/receiving circuit becomes vast, thus involving an increase in processing time. In an ordinary case, however, the ultrasound is transmitted and received using some of the transducer elements instead of using all the transducer elements. If their aperture width is narrowed, then the spatial resolution is lowered at a far distance and, therefore, the "partly cut" driving of the transducer elements is done by skipping these transducer elements in one or two interval units. Such driving promotes the generation of the grating lobe as will be set out below.

As well known, in order to cancel the grating lobe, the grating lobe is driven out of a visual range. This condition is given by:

$$EP < \lambda/(1+|\sin \theta|) \quad (1)$$

where $\theta$: the maximal deflection angle of the main lobe;

$\lambda$: the internal (inside-patient) wavelength; and

EP: the center-to-center distance between the transducer elements.

In general, the center-to-center distance EP of the transducer elements is so designed as to clear the condition. In the partly cut driving, however, the center-to-center distance EP of the transducer elements becomes effectively two- and three-times, so that the condition above cannot be cleared. As a result, the grating lobe enters into the visual field.

BRIEF SUMMARY OF THE INVENTION

It is accordingly the object of the present invention to improve the quality of an ultrasound image and go ahead with practical 3-D imaging by an ultrasound.

According to the present invention, an image is created based on harmonics components in an echo signal. The harmonics components are produced in proportion with a sound pressure. That is, many more harmonics components are produced the higher the sound pressure. Thus, the ultrasound beams are practically narrowed and the spatial resolution is improved. Further, somewhat more harmonics components are not produced from the grating lobes lower in sound pressure than the main lobe, so that the generation of the grating lobe is effectively suppressed. By doing so, the image quality is markedly improved in comparison with that by the fundamental wave.

Further, there are sometimes the cases where, with a plurality of transducer elements partly cut, the ultrasound beam is transmitted by driving the rest of the transducer elements. In this case, the grating lobe is emerging in the driving of the transducer elements in the "partly cut" fashion. The grating lobe is lower in pressure than the main lobe. The harmonics components are effectively generated at a higher sound pressure region. It is possible, as in the present invention, to reduce the artifact caused by the grating lobe by extracting harmonics components from a received signal and creating a harmonics wave image from the harmonics components.

Further, as set out above, the center-to-center distance of the drive transducer elements becomes longer than the width of the transducer elements, so that the grating lobe is liable to emerge. The grating lobe is generated at a position spaced apart by a reciprocal of the center-to-center distance of the drive transducer elements from the main lobe. If, as in the present invention, the transducer elements are partly cut in a random way, the center-to-center distance of the drive transducer elements is variable. As a result, the grating lobe is spatially dispersed, so that the artifact caused by the grating lobe is apparently lowered.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

Figure 1:
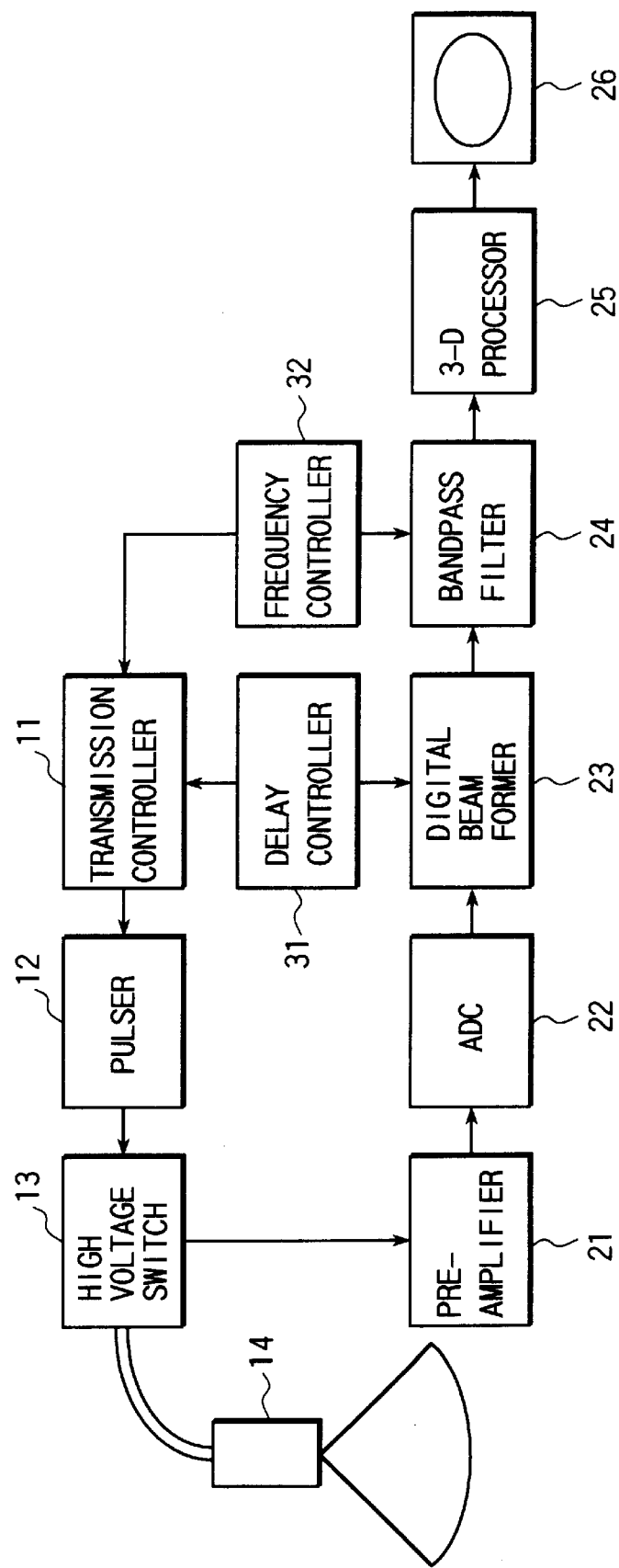
FIG. 1 is a block diagram of an ultrasound diagnostic apparatus according to a preferred embodiment of the present invention.
Figure 2:
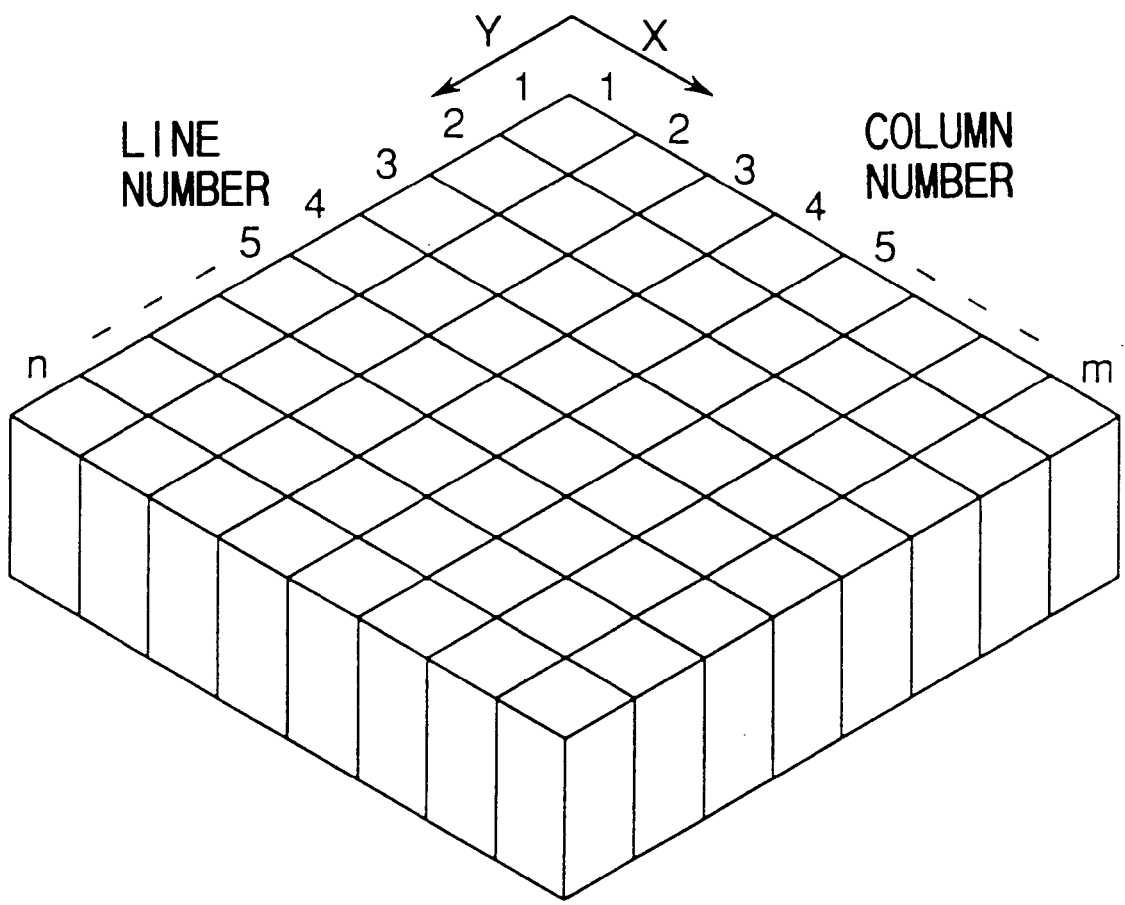
FIG. 2 is a view showing a transducer element array of an ultrasonic probe of FIG. 1.
Figure 3A:
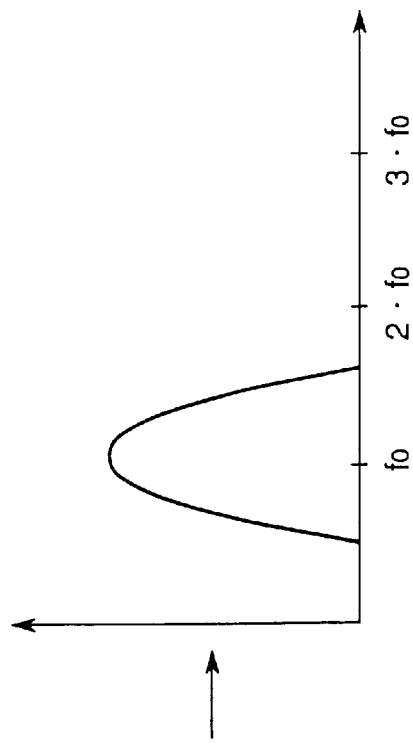
FIG. 3A is a view showing a frequency spectrum of the fundamental wave.
Figure 3A:
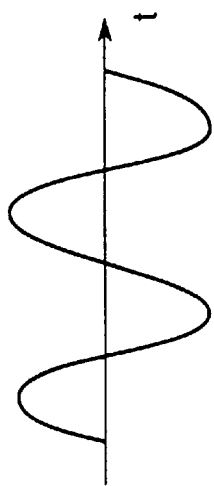
Figure 3B:
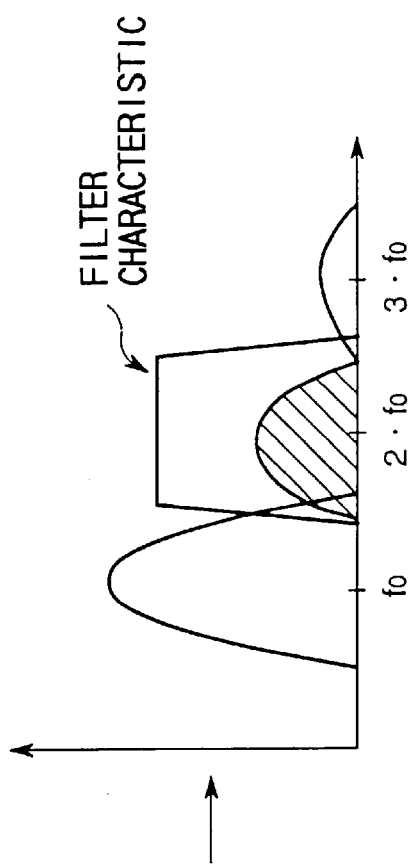
FIG. 3B is a view showing the frequency spectrum of harmonics wave and the filter characteristic of a bandpass filter in FIG. 1.
Figure 3B:
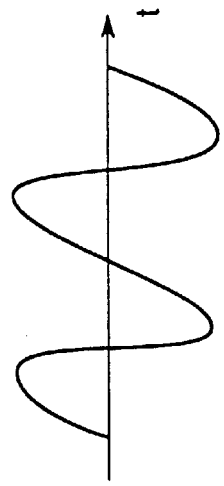

A preferred embodiment of the present invention will be explained below with reference to the drawing. FIG. 1 is a block diagram showing an ultrasound diagnostic apparatus according to an embodiment of the present invention in FIG. 1. An ultrasound probe 14 has a plurality of transducer elements for allowing the conversion to be effected between an electric energy and a sound energy. The transducer elements are arranged as a matrix array as shown in FIG. 2. A high voltage switch 13 enables a pulser 12 to be connected to the ultrasound probe 14 at a transmitting time and a pre-amplifier 21 to the probe 14 at a receiving time.

The pulser 12 has a plurality of pulser elements, connecting the pulser element to a corresponding one of the transducer element. A transmission controller 11 supplies high-frequency signal of a frequency $f_0$ individually to the respective pulser element. The respective pulse element amplifies the supplied high-frequency signal and applies it to a corresponding transducer element. The respective transducer element is oscillated by the amplified high-frequency signal. By doing so, an ultrasound wave of a center frequency $f_0$ is produced.

In order to control the timing in which the ultrasound is generated from the respective transducer element, a delay controller 31 controls the timing for outputting a high frequency signal from the transmission controller 11 to the pulser element. The timing for supplying the high-frequency signal to the respective pulser is represented by the delay pattern as will be set out below.

A frequency controller 32 controls the frequency $f_0$ of a high frequency signal outputted from the transmission controller 11, that is, controls the center frequency $f_0$ of the ultrasound. The frequency $f_0$ is adjusted to a frequency optimal to tissue harmonic imaging, that is, to a frequency with which harmonic waves are effectively generated in the living tissue.

Those echoes which are returned from the patient enable the respective transducer elements to oscillate mechanically. By doing so, a very small electric signal is produced from the respective element. The respective signal is individually amplified at the pre-amplifier. The amplified signal is supplied to an A/D converter 22 individually to a digital signal.

A digital beam former 23 is comprised of a digital circuit for realizing so-called multi-direction simultaneous reception technique. By adding the digital signals of all the transducer elements in accordance with a plurality of delay patterns, the digital beam former 23 forms a plurality of kinds of receive signals, for a single one transmission, which are different in reception directivity.

A bandpass filter 24 eliminates a fundamental wave component at and near the center frequency $f_0$ from the respective received signals and passes an integral multiple of the center frequency $f_0$, here, two-fold second harmonic components. To this end, the passband of the bandpass filter 24 is centered at $2 \cdot f_0$.

A 3-D processor 25 performs not only a normal function, such as detection, logarithmic amplification, and amplitude brilliance conversion but also a three-dimensional image data reconstruction function, such as a surface model, wire frame model or polygon model. A monitor 26 displays reconstructed three-dimensional image data.

The present invention, adopting the tissue harmonic method together with the 3-D imaging method, improves the spatial resolution and achieves a reduction of the grating lobe. By doing so, it is possible to increase the precision of the three-dimensional image. Now explanation will be given below about how the tissue harmonic imaging enables the improvement of the spatial resolution and reduction of the grating lobe.

Figure 4:
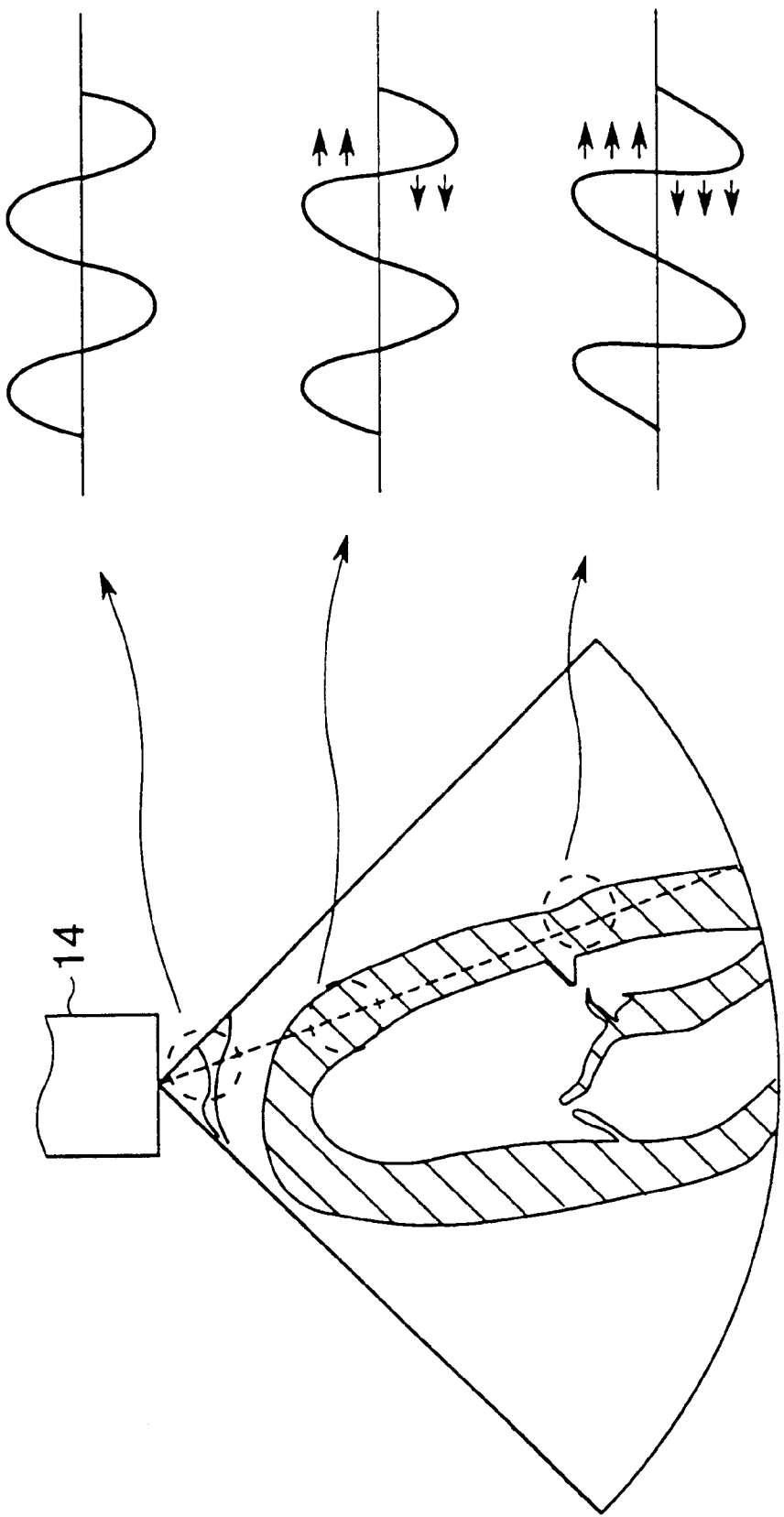
FIG. 4 is a view showing a principle on which harmonics waves are generated.

FIG. 4 shows how the waveform of the ultrasound varies in the living body. The ultrasound, being a compressional wave, propagates faster at a high pressure side than at a low pressure side. Through this nonlinear phenomenon the waveform of the ultrasound is sharp, so that harmonic waves are generated. Normally, for the tissue harmonic imaging method, use is made of two-fold second harmonic component of the center frequency $f_0$.

Figure 5:
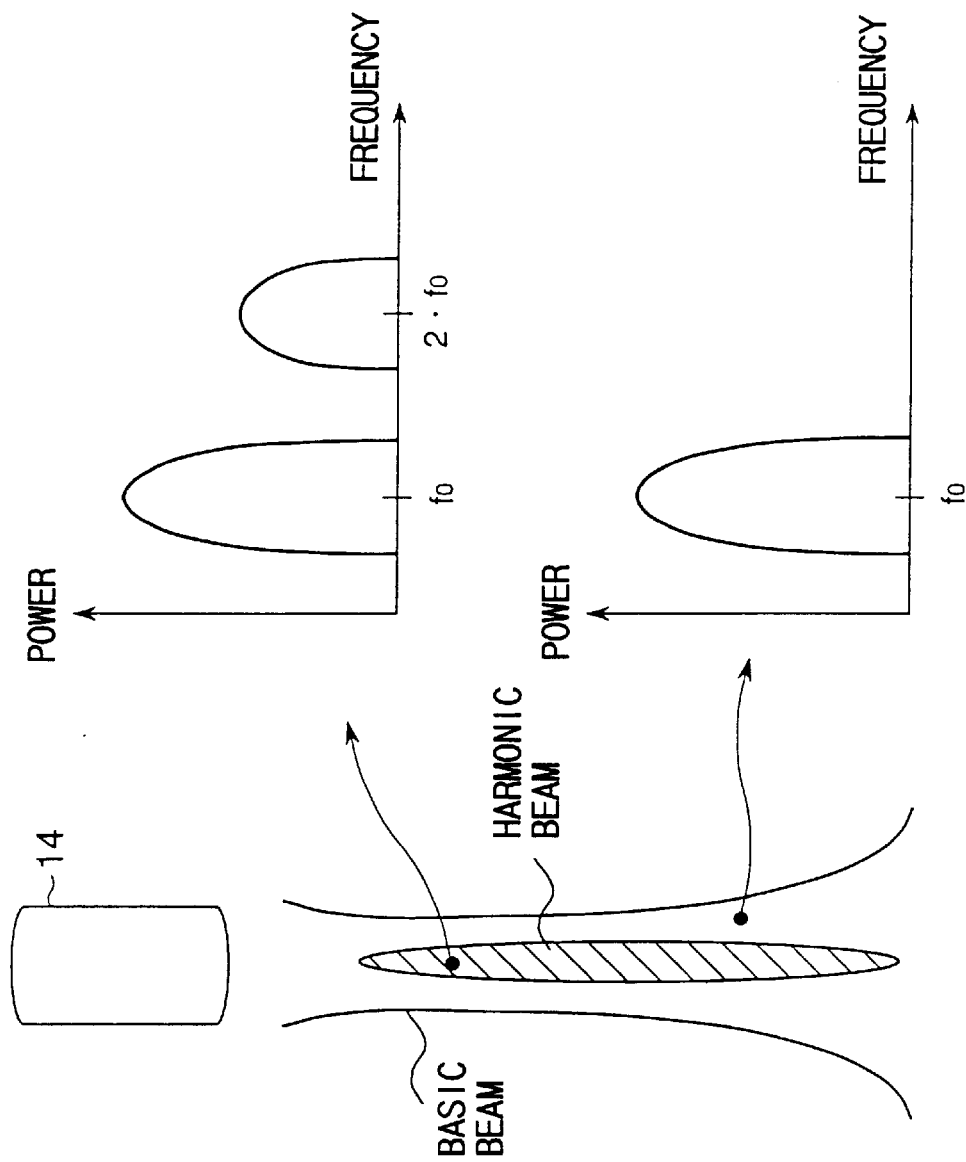
FIG. 5 is a model view showing a basic (fundamental) beam and the harmonic beam.

In consideration of on the generation principle of the harmonic wave, there occurs a pressure variation in which the generation efficiency of the harmonic waves is higher at a high sound-pressure side than at a low sound-pressure side. As shown in FIG. 5, therefore, the harmonic beam is formed as a narrow and sharp beam near the basic (fundamental) beam. Further, the grating lobe generated around the main lobe, being relatively low in sound pressure, involves almost no harmonic waves. In consequence, if image data is created based on the harmonic components, the spatial resolution is improved and, further, it is possible to remarkably decrease any artifact which is caused from the grating lobe.

Here, as already set out above, the multi-direction simultaneous reception technique is indispensable to the three-dimensional real-time imaging method. For the multi-direction simultaneous reception to be achieved it is necessary that the ultrasound beam be made artificially thick. Further, for the tissue harmonic imaging method it is necessary to raise the sound-pressure level as a whole in comparison with the ordinary ultrasound imaging method by which imaging is achieved based on the fundamental wave near the center frequency $f_0$. That is, it is necessary to provide a thick ultrasound beam of a high sound-pressure level.

Figures 6, 7:
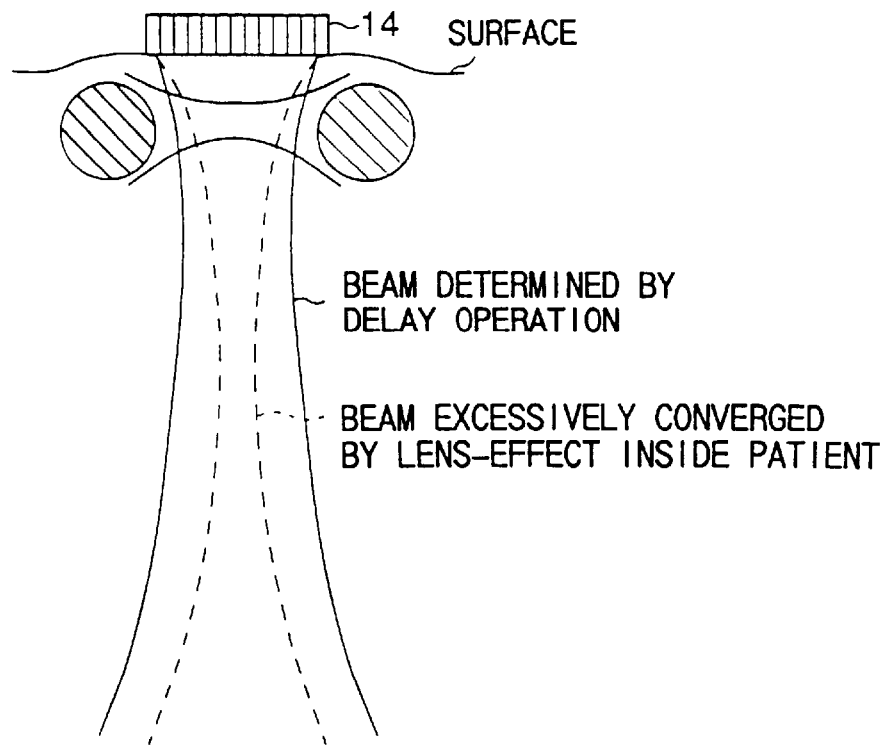
FIG. 6 is an explanatory view for explaining a lens effect of a living body.
FIG. 7 shows four groups divided by a delay control section.

However, such a thick ultrasound beam of a high sound-pressure level may have a next problem. Since there exists a region in the living body, such as the straight muscle of abdomen, producing a lens effect, there are sometimes the cases that the ultrasound beam excessively converges due to such a lens effect in the living body as shown in FIG. 6. Such an excessively converging ultrasound beam energy may exceed the safety regulations.

An explanation will be given below about how to solve an important problem relating to the safety.

The delay controller 31 divides the transducer elements of the ultrasound probe 14 into a plurality of groups, here, four groups as shown in FIG. 7. In this connection it is to be noted that these groups are not physically separated and constitute one unit from the standpoint of a transmission delay operation. The group 1 comprises odd line/odd column transducer elements. The group 2 comprises odd line/even column transducer elements. The group 3 comprises even line/odd column transducer elements. And the group 4 comprises even line/even column transducer elements.

Figure 8:
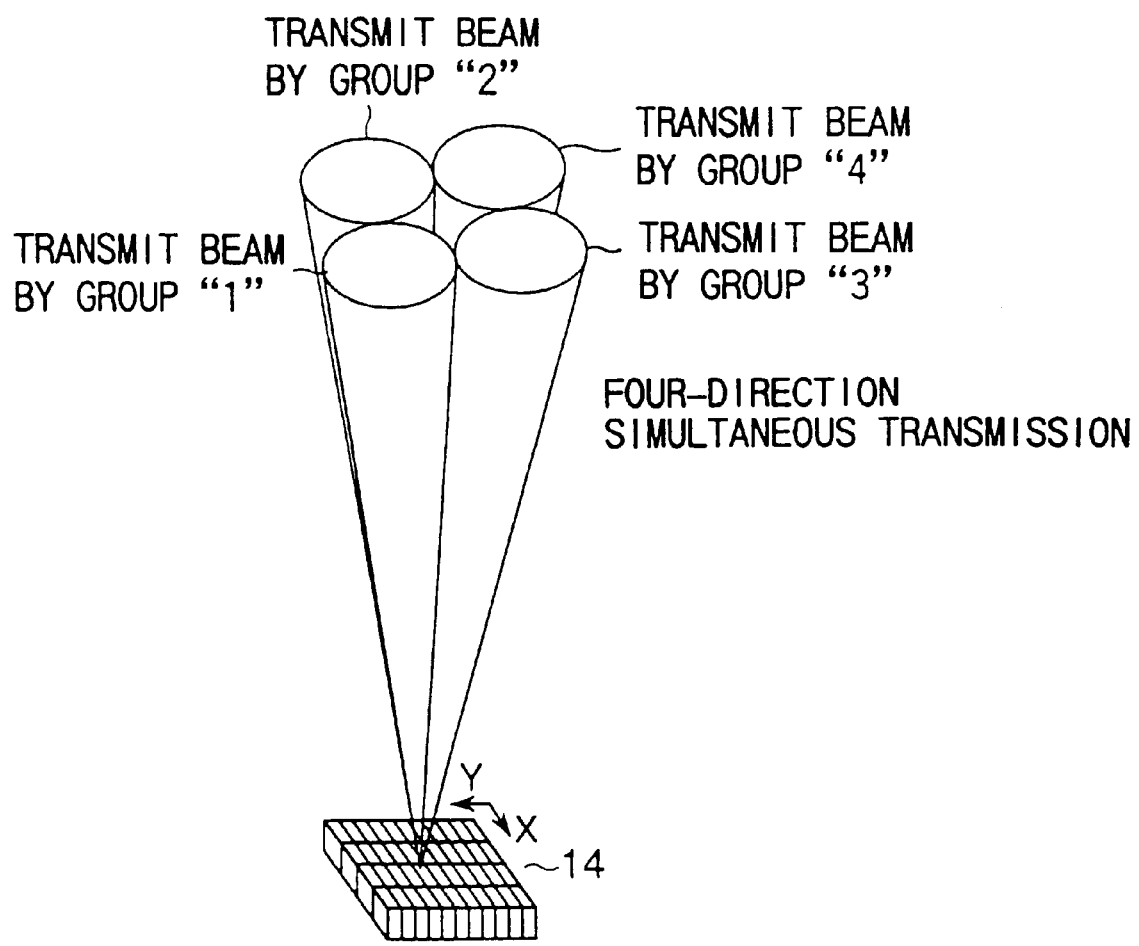
FIG. 8 shows simultaneously transmitted four ultrasound beams.
Figure 9A:
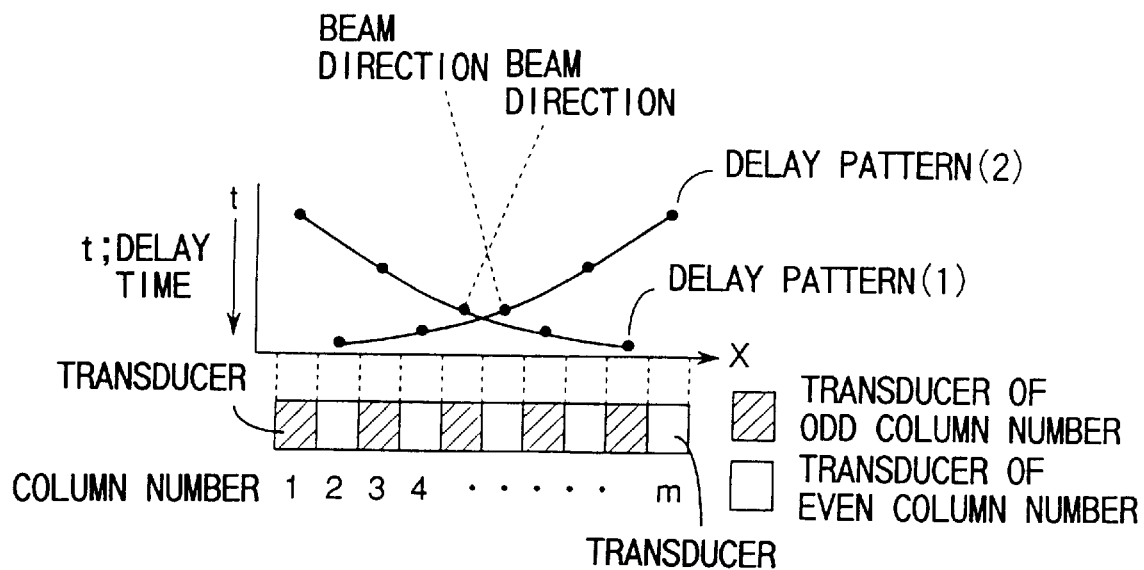
FIG. 9A is a view showing two kinds of delay patterns relating to a column direction.
Figure 9B:
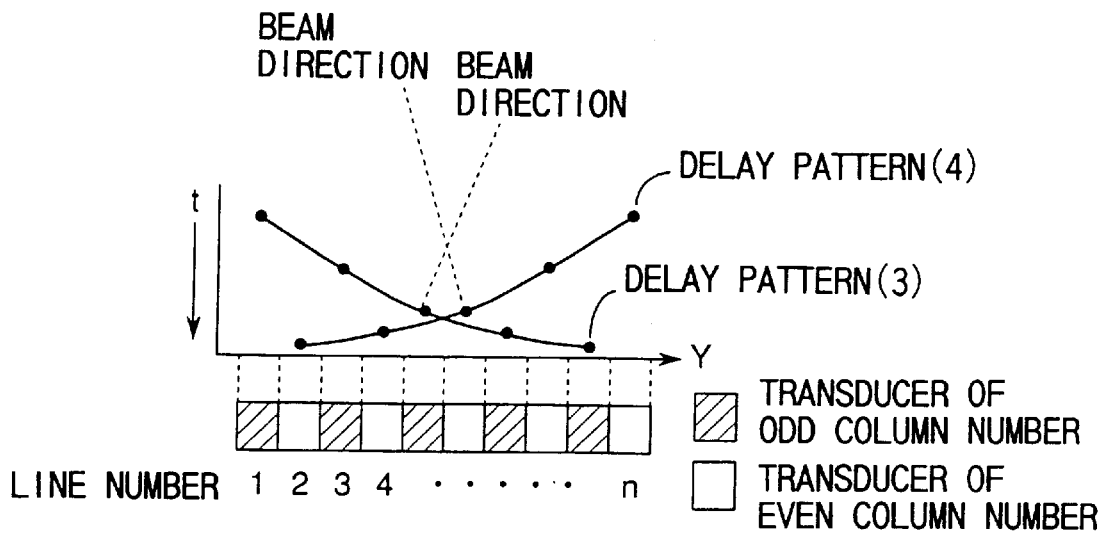
FIG. 9B is a view showing two kinds of delay patterns relating to a line direction.

From the four groups, four ultrasound beams are simultaneously transmitted as shown in FIG. 8. An optimal delay operation is done in a manner to have four ultrasound beams defined adjacent to each other. By doing so, a total sound pressure distribution of the four ultrasound beams is made thick in the same way as the sound pressure distribution of a single conventional broad beam. FIG. 9A shows two delay patterns (1) and (2) relating to the column direction X and FIG. 9B two delay patterns (3) and (4) relating to the line direction Y. These two delay patterns (1) and (2), like the two delay patterns (3) and (4), are so designed as to cross.

By a combined pattern of two delay patterns (1) and (3) an ultrasound beam is transmitted in a first direction from the group 1; by a combined pattern of two delay patterns (2) and (3) an ultrasound beam is transmitted in a second direction from the group 2; by a combined pattern of two delay patterns (1) and (4) an ultrasound beam is transmitted in a third direction from the group 3; and by a combined pattern of two delay patterns (2) and (4), an ultrasound beam is transmitted in a fourth direction from the group 4.

By replacing the single thick but high sound-pressure level ultrasound beam by combined four narrow, high sound-pressure level ultrasound beams it is possible to reduce, to a negligible extent, a risk which may be produced due to a strong lens effect caused by a synergetic effect between the delay pattern produced by a delay operation on the apparatus side and a delay pattern in the living body. The reason for this will be explained below.

Figure 10A:
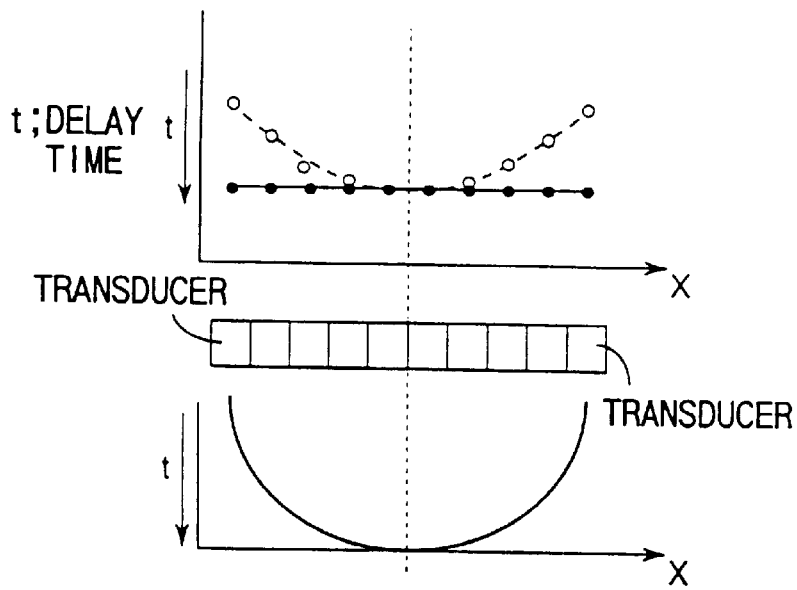
FIG. 10A is a view showing a delay pattern in a living body necessary to exhibit a strong lens effect with a delay pattern for one thick ultrasound beam.

FIG. 10A shows a delay pattern in the living body necessary to produce a strong lens effect caused by an overlay with a delay pattern for the single thick but high sound-pressure level ultrasound beam. Such a gradual monotonic delay pattern in the living body emerges at the straight muscle of abdomen, etc.

Figure 10B:
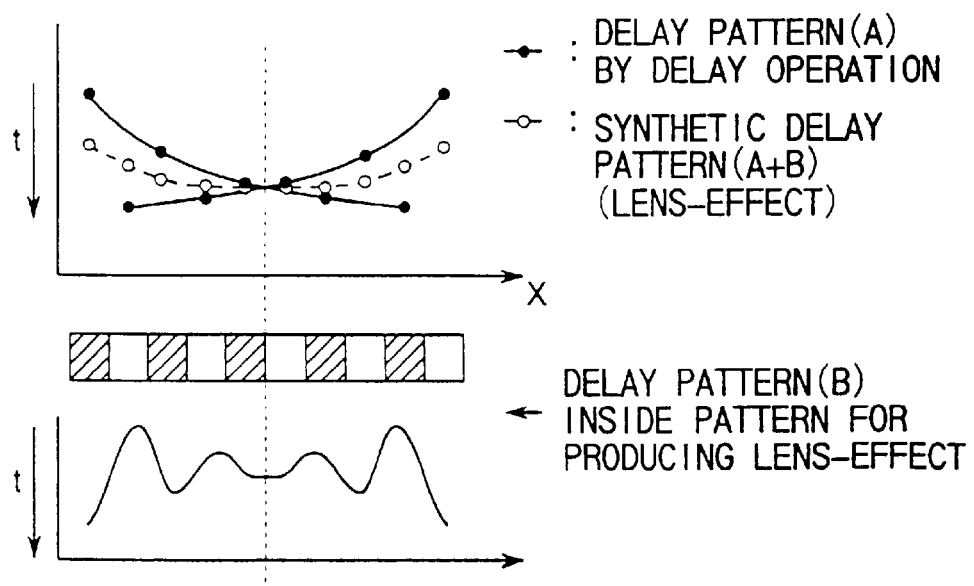
FIG. 10B is a view showing a delay pattern in a living body necessary to exhibit a strong lens effect with a delay pattern for combined four narrow ultrasound beams.

In the case where the combined four narrow, high ultrasound beams are transmitted simultaneously, a delay pattern in the living body necessary to produce a lens effect due to an overlay with a delay pattern produced on the apparatus side produces a complex but regular specific shape as shown in FIG. 10B. There is almost no possibility that such a delay pattern of a complex but regular specific shape will emerge in the living body. As a result, there occurs almost no safety problem.

Although, at the transmitting time, a plurality of ultrasound beams are transmitted in the multi-directions with the transducer elements grouped as set out above, such groups are not necessary at a receiving time. That is, a plurality of received signals are formed by subjecting those signals which are obtained from all the transducer elements to a delay operation with a plurality of delay patterns and performing an addition operation. Needless to say, the received beams are preferably adjusted to the transferred beam.

Figure 11A:
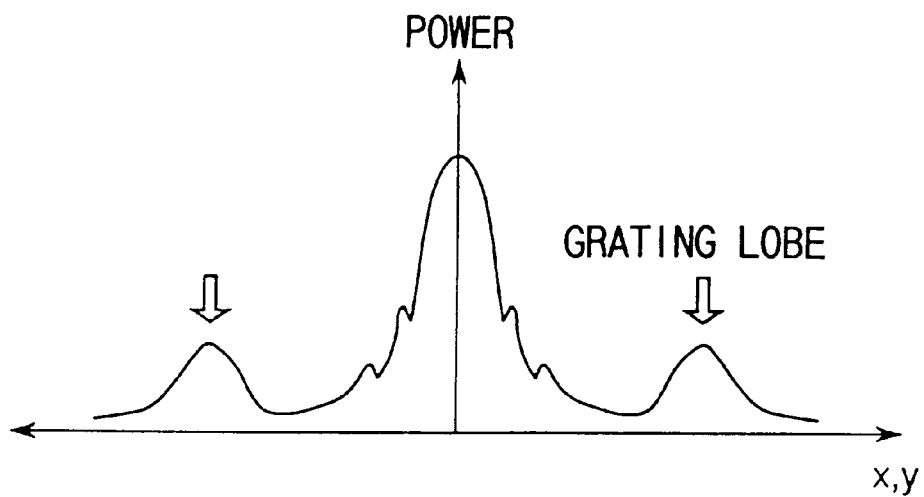
FIG. 11A is a view showing a grating lobe in a one-dimensional sound pressure distribution.
Figure 11B:
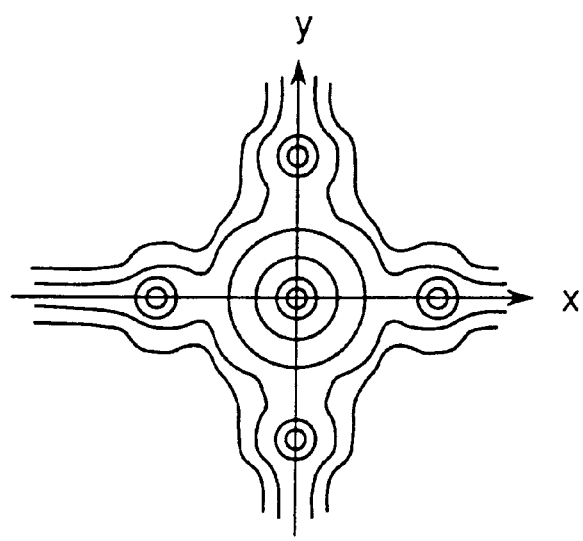
FIG. 11B is a view showing a grating lobe in a two-dimensional sound pressure distribution (contour line display)

Here, if the transducer elements are regularly grouped as shown in FIG. 7, the center-to-center distance EP of those adjacent transducer elements in the same group becomes substantially long. If the center-to-center distance EP is so long, then it is not possible to clear the condition of the equation (1). As a result, the grating lobe problem emerges as shown in FIGS. 11A and 11B. As conventionally known, the grating lobe occurs at a distance 1/EP from the center of the main lobe and, as the center-to-center distance EP of the transducer elements becomes longer, the grating lobe approaches the main lobe.

It is, however, to be noted that the grating lobe, being lower in sound pressure than the main lobe, presents never too much problem in the tissue harmonic imaging. If, for example, 10 received signals are to be formed against one transmission so as to improve the real-time characteristic, then it is necessary to transmit 10 ultrasound beams simultaneously. In this case, the center-to-center distance of the transducer elements becomes much longer and there is a possibility that the grating lobe will emerge to a not ignorable extent.

Figures 12, 13:
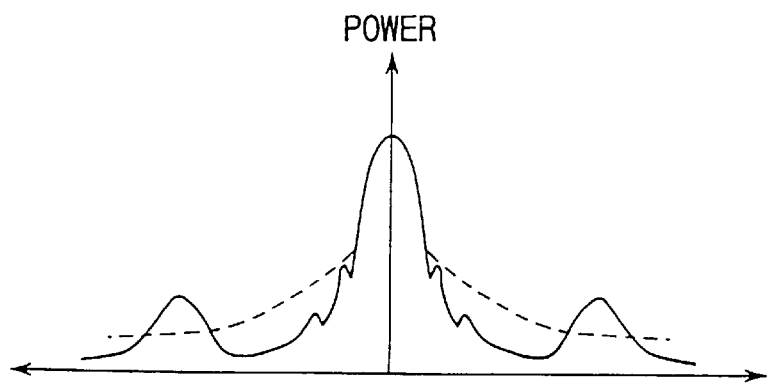
FIG. 12 shows random groupings of transducer elements effective to reduce the grating lobe.
FIG. 13 is a view showing a one-dimensional sound pressure distribution by random groups in FIG. 12.

It may be considered that the transducer elements are randomly grouped as shown in FIG. 12 so as to alleviate the grating lobe. In this case, the center-to-center distance of the transducer elements becomes variable in the same group. If the center-to-center distance of the transducer elements are not uniform, then the grating lobe is spatially dispersed as indicated by a broken line in FIG. 13 instead of converging at one spot. If the grating lobe is so dispersed, the grating lobe becomes lower in sound pressure and hence harmonic waves are never produced too much from the grating lobe.

This thought can be adopted when one ultrasound beam is transmitted by a "partly cut" drive mode. Instead of regularly driving the ultrasound elements in one or two interval units as in the prior art, some of all the transducer elements are randomly selected and driven to transmit their ultrasound beams and, by doing so, it is possible to disperse the grating lobe and suppress an adverse effect which would otherwise be produced.

Various changes or modifications of the present invention can be made without being restricted to the above-mentioned embodiment only.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnostic apparatus comprising:
   a 2D array ultrasound probe having a plurality of transducer elements arranged as a matrix array;
   a transmitting unit for supplying a high-frequency signal to the transducer element so as to transmit an ultrasound beam to a human subject;
   a receiving unit for forming a received signal of a receiving directivity from an echo signal received at the respective transducer element;
   a delay control unit for controlling the transmitting and receiving units so as to scan a three-dimensional region of interest in the human subject;
   a filter for extracting harmonic components from the received signals formed by the receiving unit in real time; and
   a processor for, based on the extracted harmonic components, creating a three-dimensional image relating to the three-dimensional region of interest in real time;
   wherein the receiving unit forms a plurality of received signals of different receiving directivities after one transmission and the transmitting unit simultaneously transmits a plurality of ultrasound beams of different transmitting directivities.

2. An ultrasound diagnostic apparatus according to claim 1, wherein the delay control unit properly uses a plurality of delay patterns for respective transducer elements.

3. An ultrasound diagnostic apparatus according to claim 2, wherein the delay control unit irregularly a different delay pattern to a plurality of groups into which the transducer elements are divided.

4. An ultrasound diagnostic apparatus according to claim 3, wherein the delay control unit applies a first delay pattern to an odd line/odd column transducer element, a second delay pattern to an odd line/even column transducer elements, a third delay pattern to an even line/odd transducer element and a fourth delay pattern to an even line/even column transducer element.

5. An ultrasound diagnostic apparatus according to claim 1, wherein the filter has a passband set to allow a two-fold secondary harmonic component of a center frequency of the transmitted ultrasound beam to be mainly extracted.

6. An ultrasound diagnostic apparatus comprising:
   an ultrasonic probe having a plurality of transducer elements arranged as a matrix;
   a transmitting unit which, in order to transmit an ultrasound beam to a human subject, drives the transducer elements while partly cutting the transducer elements in a random fashion;
   a receiving unit for forming a received signal of a receiving directivity from an echo signal received at the respective transducer element; and
   a processor for creating an ultrasound image from the received signal formed by the receiving unit.

7. An ultrasound diagnostic apparatus comprising:
   an ultrasound probe having a plurality of transducer elements;
   a transmitting unit which, in order to transmit an ultrasound beam to a human subject, drives the transducer elements while partly cutting the transducer elements;
   a receiving unit for forming a received signal of a receiving directivity from an echo signal received at the respective transducer element;
   a filter for extracting harmonic components from the received signal formed by the receiving unit; and
   a processor for creating an ultrasound image based on the extracted harmonic components.

* * * * *